United States Patent [19]

Knudtson et al.

[11] Patent Number: 4,524,628
[45] Date of Patent: Jun. 25, 1985

[54] IN LINE DRY MATERIAL SAMPLER

[75] Inventors: Lynn A. Knudtson, Omaha, Nebr.; Glenn R. Sprenger, Lakeland, Fla.

[73] Assignee: Stauffer Chemical Company, Westport, Conn.

[21] Appl. No.: 665,814

[22] Filed: Oct. 29, 1984

Related U.S. Application Data

[63] Continuation of Ser. No. 291,680, Aug. 10, 1981, abandoned, which is a continuation-in-part of Ser. No. 119,267, Feb. 7, 1980, abandoned.

[51] Int. Cl.³ .............................................. G01N 1/20
[52] U.S. Cl. ................................................ 73/863.43
[58] Field of Search ........................ 73/863.43, 863.45

[56] References Cited

U.S. PATENT DOCUMENTS

| | | | |
|---|---|---|---|
| 398,275 | 2/1889 | Palmer | 73/863.43 |
| 2,405,486 | 8/1946 | Bauer | 73/863.43 |
| 2,670,629 | 3/1954 | Belden | 73/863.43 |
| 3,942,388 | 3/1976 | Rathnow | 73/863.43 |

FOREIGN PATENT DOCUMENTS

| | | | |
|---|---|---|---|
| 1049127 | 1/1959 | Fed. Rep. of Germany | 73/863.43 |
| 0996926 | 12/1951 | France | 73/863.43 |
| 1295132 | 4/1962 | France | 73/863.43 |

Primary Examiner—S. Clement Swisher
Attorney, Agent, or Firm—Vivienne T. White

[57] ABSTRACT

A continuous in line dry material sampler for sampling dry flowing material within a manufacturing or transported stream comprising a series of concentrically nested stages having no moving parts and having means for obtaining a representative proportional sample of the material as it flows through the sampler.

7 Claims, 3 Drawing Figures

U.S. Patent  Jun. 25, 1985  4,524,628
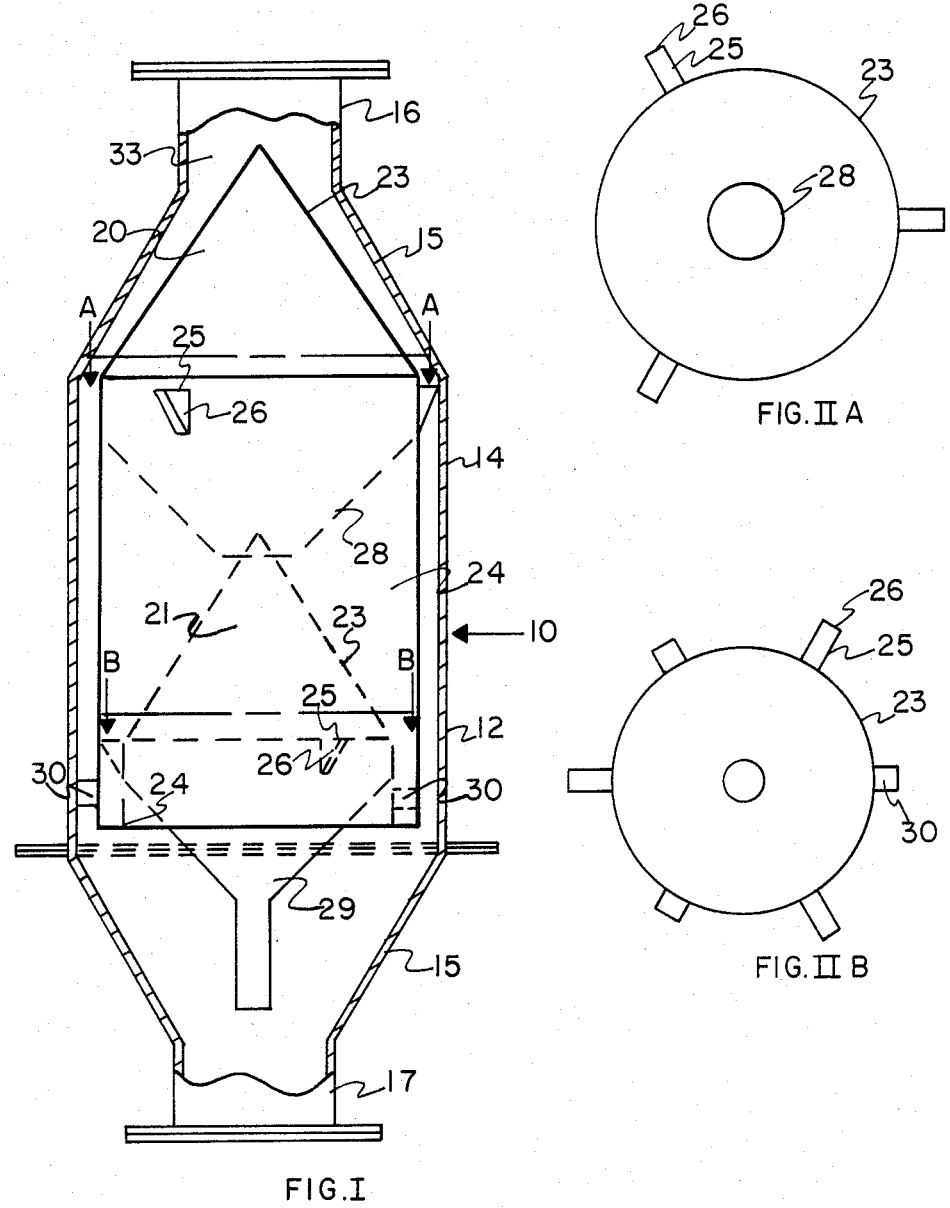
FIG. I
FIG. II A
FIG. II B

IN LINE DRY MATERIAL SAMPLER

CROSS REFERENCE TO RELATED APPLICATION

This is a continuation of application Ser. No. 291,680, filed Aug. 10, 1981, now abandoned, which is a continuation-in-part of application Ser. No. 119,267, filed Feb. 7, 1980, now abandoned.

BACKGROUND OF THE INVENTION

1. Field of the Invention

The invention relates to a continuous in line sampling device for obtaining a representative sample of dry freely flowing material within a manufacturing or transported stream.

2. Prior Art

In the manufacturing of dry particulate materials, it is frequently necessary for quality control purposes to determine by physical or chemical analysis, the quality of small samples. Obviously, very small deviations from specification, in the analysis, can have profound effects on decisions regarding the value or acceptability of the material. A critical step in providing an accurate analysis of such material is to obtain a representative sample.

A sample is usually taken from a feed stream of material in free fall as it passes through a relatively large pipe or chute. Since particulate matter may segregate as it passes through a pipe or chute, for instance, because of differences in particle size or particle density, it is advantageous to obtain a representative sample across the entire cross-section of the sample stream. Obtaining such a sample is the function of a primary sampling device.

Sampling devices are commercially available in a variety of designs.

U.S Pat. No. 2,405,486, for instance, discloses a sampling machine comprised of a movable cone seated on a stationary cone in a nested relationship each cone having a plurality of openings forming splitters. The movable cone having control rods for fully aligning or partially aligning the splitters of the cones and the size of the splitters.

A random sampling machine disclosed as having no moving or rotating parts is described in U.S. Pat. No. 2,405,951 to Herrold. The sampler is said to provide a desired percentage of a material that is selected at random. The sampler as disclosed comprises a mixing chamber having a plurality of concentric conical material-deflecting plates (which may be of differing diameters) alternately concave upward and downward and having staggerd openings for deflecting the falling material in a random manner. The splitting of the proportional sample disclosed in the patent is accomplished after the material leaves the last plate and just prior to its entering a hopper.

It is an object of the present invention to provide a sampler which is simple to construct, involves no moving or rotational parts and which directly provides a small representative sample of the material being sampled.

BRIEF DESCRIPTION OF THE DRAWINGS

FIG. I is a longitudinal, sectional view of the sampling device in accordance with the invention.

FIGS. IIA and B are sectional views of FIG. I taken along lines A—A and B—B.

SUMMARY OF THE INVENTION

In accordance with the stated objectives, a sampling device is disclosed which is of simple construction having no moving parts and which directly provides a small representative sample of the material being sampled. The sampling device is comprised of a series of concentrically nested stages in a housing; each stage of the concentrically nested stages being comprised of a cylinder with a cone attached at one end to form the top of the stage, the cylinder having a plurality of openings and a plurality of angled chutes positioned to direct material passing over the cone into the openings, the chutes being arranged around the circumference of the cylinder, each stage except one having means for conveying the material entering the stage to the conical surface of the next stage, the excepted stage having means for conveying the sample out of the sampling zone.

The construction and arrangement of the sampling device is better disclosed and explained in connection with the accompanying drawings.

DETAILED DESCRIPTION OF THE INVENTION

The invention is directed to a device for obtaining a small representative sample of a freely flowing material.

The term "nested" is used herein to mean that the conical portion of each stage projects sufficiently into the outlet of the previous stage to allow the material flowing therethrough to fall only onto the conical surface and not around it.

FIG. I illustrates a longitudinal side view of an embodiment of the sampling device of the invention. The sampling device 10 is comprised of a housing 12 generally consisting of a cylinder 14 with cones 15 truncated at their pointed ends and affixed to the cylinder 14. To the truncated ends of the cones 15 is attached cylinders 16 and 17 having flanged ends through which the free flowing materials enters and leaves the sampler.

Internally, the sampler in the embodiment shown is comprised of a series of concentrically nested stages. As illustrated in FIG. 1, two stages are presented, an upper stage 20 and a lower stage (nested) 21. Each stage is comprised of a cone 23, the conical end of which can be rounded or pointed, engaged with one end of a cylinder 24 to form the top of the stage. The cylinder 24, of each stage having a plurality of openings 25, and having chutes or splitters 26 positioned adjacent to the openings for splitting or cutting a desired portion of the material flowing over the conical surface, and directing the split or cut portion of the material to the interior of the stage through openings 25. Positioned within the cylinder 24 of the upper stage 20, just below the openings 25, is a stemless funnel 28 which comprises the means whereby the cut material entering the stage 20 through the opening 25, is conveyed to stage 21. A stemmed funnel 29 positioned within cylinder 24 of stage 21 just below openings 25 collects the material cut by the chutes 26 of the stage, and conveys the cut material entering that stage out of the sampling zone.

The number and size of the openings 25, chutes 26, and the concentrically nested stages determine the size of the final sample collected in relation to the amount of material passing through the sampler. In the embodiment shown in FIG. IIA and FIG. IIB, each stage has three openings, and chutes 26 affixed thereto which are disposed at 120° spacings around the cylindrical surface 24. The chutes 26 of the upper stage 20 are at about a 60° variance from the chutes of the lower stage 21 so as to increase the quality of the sample obtained.

The surface of the cone 23 is at about 60° angle from the horizontal and the surface of the funnel 28 and 29 are at about a 45° angle from the horizontal. The angles of inclination of the funnel and cones are not critical but are generally at least steeper than the angle of repose of the material being sampled. The preferred angles are dependent on the specific application. It should be evident to one having skill in the art that the continuous sampling device disclosed herein, which can be disposed within a manufacturing process line, may include as many stages as a particular application dictates until the desired sample size is obtained.

The sampler operates as follows: as the material being sampled enters the sampler, it is distributed around the area between the sampler housing 12 and the upper stage 20 by the conical surface 23 of this stage. The chutes 26 of stage 20 cut or split a portion of the material and diverts the cut portion through the funnel 28 onto the conical surface 23 of the lower stage 21. The remaining material passes through the sampling zone in the area between cylinder 14 and cylinder 24 of the first stage. As a result, the portion of the sample cut by stage 21 is further cut by the chutes 26 of stage 21 prior to flowing directly from the sampler or sampling zone through funnel 29. It should be evident from the drawings that the diameter of the stages decreases serially. Upper stage 20, therefore, has a greater diameter than stage 21 as shown in FIGS. IIA and IIB. The portion of the dry sample material not cut at any stage of the sampling process is prevented from reentering any of the subsequent stage chutes by the cylinder 24 of each stage which as shown in FIG. I, all extend beyond the chutes of the final stage 21. The cylinder 24 of each stage also serve to retain the stages in their serially nested relationship. Interspaced between the cylinders 24 of each stage at a point below the chutes of the final stage are small retaining blocks 30 bolted or otherwise affixed to the cylinder of the previous stage which hold the stages in their relative position to one another. The cylinder of the first stage is likewise bolted or affixed to the cylinder 14 of the housing. The blocks, which in FIG. IIB of the embodiment shown are spaced at a 60° distance from each other, allow the freely falling material, not entering the chutes of the previous stage, to pass unhindered from the sampler into the main production stream through cylinder 17 of the housing 12. Similarly, the chutes of each stage can be welded to the cylinder portion 24 of the previous stage, and, therefore, also maintain the stages in position. The chutes of the first stage 20 can be welded or otherwise affixed to the cylinder 14 of the housing.

It should be evident to one having skill in the art that in order to obtain a representative sampling of the flowing material, the sizing of the internal nested stages relative to the housing and to each other should be such as to maximize and equalize the flow of material onto the conical surfaces 23, 23 and through the sampler.

In the embodiment shown, for instance, the donut area 33 between the apex of the first stage 20 and the cylindrical surface 16 of the housing 14 is about equal to the cross-sectional area of the pipe (not shown) conveying the material to the sampler, so that the materials flows first onto the conical surface 23 and not directly through the area between the cylinder 14 and the first stage cylinder 24. Each stage in the embodiment shown was found to split about 10 percent of the material flowing onto its conical surface 23.

The dimensions stated in this disclosure and illustrated in the drawings are not critical for the construction of a sampler in accordance with the disclosure. The size of the individual parts, and the materials used to construct the parts of the sampler may be varied according to application. Some materials found suitable for use in constructing the parts disclosed herein were aluminum or stainless steel, especially where corrosive materials were being sampled. The use of plastic material can cause a build-up of static electricity, which can cause fines to adhere to the surfaces and fouling of the sampler. Plastic materials treated to reduce buildup of static charges can be used in practicing the invention.

While there has been shown and described herein, preferred embodiments of the invention, it will be understood that modifications and changes may be made without departing from the spirit and scope thereof as will be clear to those having skill in the art.

What is claimed is:

1. A sampling device for obtaining a representative sample of freely flowing material comprised of a series of concentrically nested stages in a housing; each stage of the concentrically nested stages being comprised of a cylinder with a cone attached at one end to form the top of the stage, the cylinder having a plurality of openings, and a plurality of angled chutes positioned to direct material passing over the cone into the openings, the chutes being arranged around the circumference of the cylinder, each stage except one having a stemless funnel containing an outlet for conveying the material entering the stage to the conical surface of the next stage, which projects into the outlet of the stemless funnel, the excepted stage having means for conveying the sample out of the sampling zone.

2. The sampling device of claim 1 comprised two concentrically nested sampling stages.

3. The sampling device of claim 1 wherein the stages are comprised of three chutes to direct the materials passing over the cone into the openings.

4. The sampling device of claim 3 wherein the chutes of the stages are disposed at a 120° spacings around the cylinder.

5. The sampling device of claim 1 wherein the chutes of the concentrically nested stages are at about a 60° variance from each other.

6. The sampling device of claim 1 wherein the means for conveying the material out of the sampling zone is a stemmed funnel.

7. The sampling device of claim 1 wherein the concentrically nested stages are maintained in their nested relationship by bolts.

* * * * *

UNITED STATES PATENT AND TRADEMARK OFFICE
CERTIFICATE OF CORRECTION

PATENT NO. : 4,524,628

DATED : June 25, 1985

INVENTOR(S) : L. A. Knudtson et al.

It is certified that error appears in the above—identified patent and that said Letters Patent is hereby corrected as shown below:

Col. 1, line 53, change "staggerd" to -- staggered --; and

Col. 4, line 45, change "comprised" to -- comprising --.

Signed and Sealed this

Twenty-ninth Day of July 1986

[SEAL]

Attest:

DONALD J. QUIGG

Attesting Officer     Commissioner of Patents and Trademarks